United States Patent
Davenport et al.

(10) Patent No.: US 10,793,890 B2
(45) Date of Patent: Oct. 6, 2020

(54) APPARATUS FOR DETECTING ATP IN A LIQUID SAMPLE

(71) Applicant: 3M INNOVATIVE PROPERTIES COMPANY, St. Paul, MN (US)

(72) Inventors: Kenneth R. Davenport, Hammond, WI (US); Mark B. Driscoll, Pontypridd (GB); Rachel E. Evans, Bridgend (GB); Catherine M. Ramsay, Cowbridge (GB); Neil Percy, St. Paul, MN (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 1407 days.

(21) Appl. No.: 14/410,718

(22) PCT Filed: Jul. 1, 2013

(86) PCT No.: PCT/US2013/048848
§ 371 (c)(1),
(2) Date: Dec. 23, 2014

(87) PCT Pub. No.: WO2014/008150
PCT Pub. Date: Jan. 9, 2014

(65) Prior Publication Data
US 2015/0322481 A1    Nov. 12, 2015

Related U.S. Application Data

(60) Provisional application No. 61/668,520, filed on Jul. 6, 2012.

(51) Int. Cl.
*C12Q 1/00* (2006.01)
*G01N 1/10* (2006.01)
(Continued)

(52) U.S. Cl.
CPC .............. *C12Q 1/008* (2013.01); *C12Q 1/66* (2013.01); *G01N 1/02* (2013.01); *G01N 1/10* (2013.01);
(Continued)

(58) Field of Classification Search
CPC . C12Q 1/008; C12Q 1/66; G01N 1/10; G01N 1/02; G01N 2001/028; B01L 3/5029
See application file for complete search history.

(56) References Cited

U.S. PATENT DOCUMENTS 3,169,905 A    2/1965 Lambert
3,792,699 A    2/1974 Tobin et al.
(Continued)

FOREIGN PATENT DOCUMENTS

CN    101464412    6/2009
EP    0 105 747    4/1984
(Continued)

OTHER PUBLICATIONS

Cosby, N. et al. "Custom Enzyme Substrates for Luciferase-based Assays"; Cell Notes; Issue 18, 2007; pp. 9-11.
(Continued)

*Primary Examiner* — Gautam Prakash
(74) *Attorney, Agent, or Firm* — Eric E. Silverman

(57) ABSTRACT

An apparatus (1000) and kit (1000) for the detection of ATP in a liquid sample is provided. The apparatus and kit comprise a liquid reagent composition comprising luciferin and a sampling device having (100) a sampling portion (30) and a handling portion (20). The sampling portion (30) is adapted to acquire and releasably retain a predetermined volume of a liquid sample in one or more cavity (32) that is not substantially defined by space between a plurality of fibers. The sampling device (30) comprises a dry coating that includes an effective amount of a pH-adjusting reagent
(Continued)

that, when contacted with a liquid reagent composition having a pH of about 6.8 or lower, changes the pH of the liquid reagent composition to 6.9 or higher. A method of use of the apparatus or kit is also provided.

18 Claims, 3 Drawing Sheets

(51) Int. Cl.
 *C12Q 1/66* (2006.01)
 *G01N 1/02* (2006.01)
 *B01L 3/00* (2006.01)
(52) U.S. Cl.
 CPC ...... *B01L 3/5029* (2013.01); *G01N 2001/028* (2013.01)

(56) References Cited

U.S. PATENT DOCUMENTS

| | | | |
|---|---|---|---|
| 3,864,085 A * | 2/1975 | Woodbridge | G01N 33/52 436/86 |
| 4,013,416 A | 3/1977 | Rittersdorf et al. | |
| 4,036,213 A | 7/1977 | Karuhn | |
| 4,775,626 A * | 10/1988 | Armenta et al. | C12M 23/08 435/189 |
| 4,978,504 A | 12/1990 | Nason | |
| 5,266,266 A | 11/1993 | Nason | |
| 5,827,675 A | 10/1998 | Skiffington et al. | |
| 5,879,635 A | 3/1999 | Nason | |
| 5,965,453 A | 10/1999 | Skiffington et al. | |
| 6,180,395 B1 | 1/2001 | Skiffington et al. | |
| 6,383,804 B1 | 5/2002 | Ward, Jr. et al. | |
| 6,524,530 B1 | 2/2003 | Igarashi et al. | |
| 6,548,018 B2 | 4/2003 | DiCesare et al. | |
| 6,867,342 B2 | 3/2005 | Johnston et al. | |
| 7,399,984 B2 | 7/2008 | Feldsine et al. | |
| 7,494,781 B1 | 2/2009 | Charm et al. | |
| 7,556,933 B2 | 7/2009 | Cairns et al. | |
| 8,114,027 B2 | 2/2012 | Triva | |
| 8,158,412 B2 * | 4/2012 | Porat et al. | C12M 23/08 422/500 |
| 2002/0057991 A1 | 5/2002 | Kelly et al. | |
| 2003/0165550 A1 | 9/2003 | Rhoades | |
| 2004/0267181 A1 | 12/2004 | Tuite et al. | |
| 2006/0073537 A1 | 4/2006 | Cairns et al. | |
| 2006/0216196 A1 | 9/2006 | Satoh et al. | |
| 2011/0179887 A1 | 7/2011 | Cobian et al. | |
| 2011/0262951 A1 | 10/2011 | Young et al. | |
| 2011/0262952 A1 | 10/2011 | Young et al. | |
| 2012/0009588 A1 | 1/2012 | Rajagopal et al. | |
| 2012/0100531 A1 | 4/2012 | Rajagopal et al. | |

FOREIGN PATENT DOCUMENTS

| | | |
|---|---|---|
| EP | 1 333 097 | 8/2003 |
| GB | 1 371 417 | 10/1974 |
| GB | 2 358 061 | 7/2001 |
| JP | 2000-253899 | 9/2000 |
| JP | 2000-319280 | 11/2000 |
| WO | WO 1993/00994 | 1/1993 |
| WO | WO 1994/11528 | 5/1994 |
| WO | WO 1997/03209 | 1/1997 |
| WO | WO 1997/23596 | 7/1997 |
| WO | WO 1998/55094 | 12/1998 |
| WO | WO 2000/61105 | 10/2000 |
| WO | WO 2000/61106 | 10/2000 |
| WO | WO 2000/61107 | 10/2000 |
| WO | WO 2001/054552 | 8/2001 |
| WO | WO 2003/050513 | 6/2003 |
| WO | WO 2006/069053 | 6/2006 |
| WO | WO 2007/069240 | 6/2007 |
| WO | WO 2009/134509 | 11/2009 |
| WO | WO 2009/140356 | 11/2009 |
| WO | WO 2010/129726 | 11/2010 |
| WO | WO 2014/007846 | 1/2014 |

OTHER PUBLICATIONS

Gürtler, V. et al.; "New approaches to typing and identification of bacteria using the 16S-23S rDNS spacer region"; Microbiology; vol. 142; 1996; pp. 3-16.
Rose, L. et al.; "Swab Materials and *Bacillus anthracis* Spore Recovery from Nonporous Surfaces"; Emerging Infectious Diseases; vol. 10, No. 6; 2004; pp. 1023-1029.
Brochure from Kensington Computer Products Group entitled "Surface Guardian® Cleaning Swabs" 2008; 1 pg.
Brochure from Professional Disposal International entitled "Nice Pak, The Global Leader in pre-Moistened Wipes: Healthcare Information" 2008; 3 pgs.
Brochure from COPAN Diagnostics Inc. entitled "SRK Environmental Swab Systems" 8 pgs.
Web page entitled Copan Flocked Swabs; Copan Diagnostics, Inc. [retrieved from the internet on Jul. 13, 2012], URL www.copanusa.com/index.php/products/flocked-swab/ ; 1 pg.
Technical Bulletin No. BL-100 entitled "Bioluminescent Determination of ATP with Luciferase-Luciferin"; from Sigma Chemical Company; 1991; 6 pgs (XP055062780).

* cited by examiner

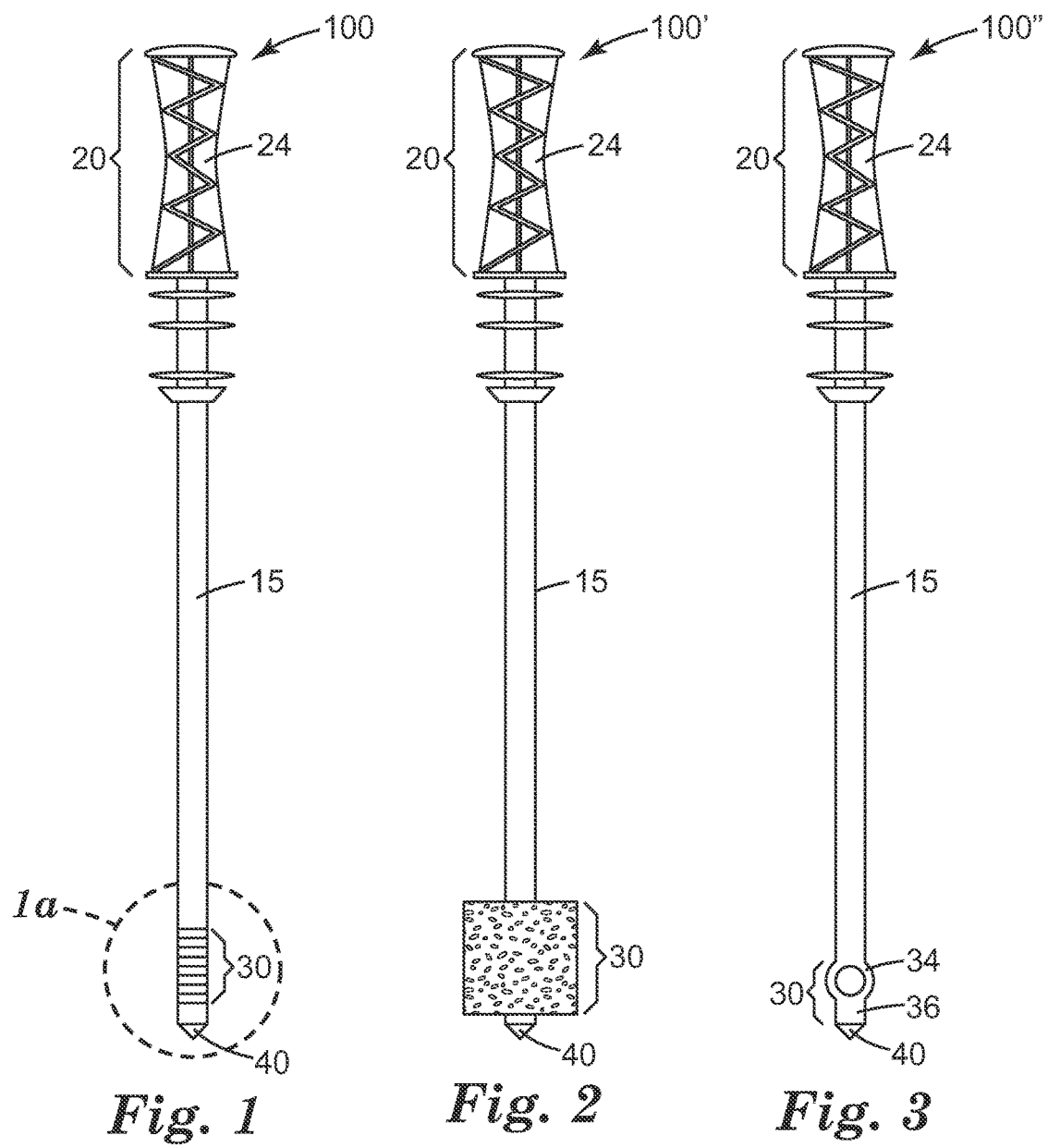
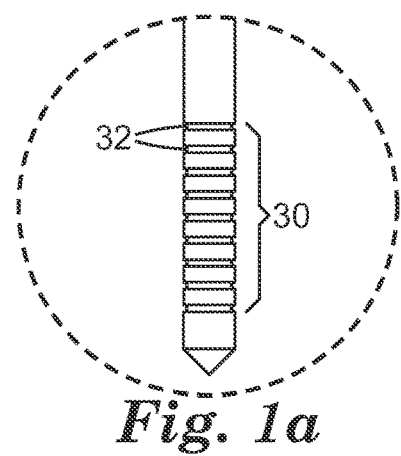
Fig. 1  Fig. 2  Fig. 3
Fig. 1a

APPARATUS FOR DETECTING ATP IN A LIQUID SAMPLE

CROSS REFERENCE TO RELATED APPLICATIONS

This application is a national stage filing under 35 U.S.C. 371 of PCT/US2013/048848, filed Jul. 1, 2013, which claims priority to U.S. Provisional Patent Application No. 61/668,520, filed Jul. 6, 2012, the disclosure of which is incorporated by reference in its entirety herein.

BACKGROUND

Sampling programs are used to monitor critical raw materials, in-process materials, finished goods, and processing environments in the food and beverage industry. Routine sampling and testing can allow quality assurance personnel to detect undesirable materials, such as microorganisms, at a very early stage and take steps to prevent subsequent contamination of equipment and/or products. A variety of tests can be performed to detect the unwanted materials. Examples of such tests include chemical residue tests (e.g., Adenosine triphosphate (ATP) bioluminescence tests and protein colorimetric tests), culture methods, genetic tests (e.g., PCR), immunodiagnostic tests, and bioluminescent tests.

Sample-collection devices typically are used to collect surface samples for environmental tests. Commercially-available sample-collection devices include absorbent devices such as sponges, swabs, and the like. In addition, certain sample-collection devices are capable of collecting a predetermined volume of a liquid sample.

ATP is used routinely to detect a presence or absence of microorganisms in a sample. The chemical energy produced from the breakdown of ATP is converted into light energy. Each molecule of ATP consumed in the reaction produces one photon of light. This light output can be quantified in a luminometer. The presence of ATP in a sample may be a direct indicator of the presence of a microorganism (i.e., the ATP is derived from a microorganism) or the ATP may be an indirect indicator of the presence of a microorganism (i.e., the ATP is derived from vegetative or animal matter and indicates that nutrients that support the growth of microorganisms may be present in the sample). In addition, the presence or absence of ATP in a sample is used routinely to assess the efficacy of cleaning processes in food, beverage, other industrial processed, healthcare (e.g. endoscopes) and for such as cooling and process waters and/or to determine whether biocide treatment has been effective in reducing the level of microorganisms.

SUMMARY

The present disclosure generally relates to the detection of ATP in a sample using luciferase enzyme. In particular, the disclosure relates to a multi-purpose sampling device that comprises a dry coating comprising a pH-adjusting reagent. The pH-adjusting reagent is capable of causing a pH change when contacted with a liquid reagent composition comprising luciferin. The pH change can facilitate the achievement of a substantially steady-state light-emitting reaction in a shorter period of time than at a lower pH. Surprisingly, the sampling device can be contacted with a liquid sample and, even though the dry coating may be soluble in the liquid sample, an effective amount of the pH-adjusting reagent is retained on and/or in the sampling device and the effective amount can be transferred to the liquid reagent composition where it effects the aforementioned pH change. In addition, the sampling device obtains a predetermined volume of a liquid sample, thereby permitting the operator to detect and, optionally, quantitate the amount of ATP in the liquid sample.

In one aspect, the present disclosure provides a kit. The kit can comprise a container with an opening and a cuvette portion that is adapted to be operationally coupled to a luminometer, a liquid reagent composition comprising luciferin, and a sampling device having a sampling portion. The liquid reagent composition can be disposed in a closed compartment. The pH of the liquid reagent composition is about 6.8 or lower. The sampling portion of the sampling device is adapted to acquire and releasably retain a predetermined volume of a liquid sample in one or more cavity that is not substantially defined by space between fibers. The sampling device can comprise a dry coating that includes an effective amount of a pH-adjusting reagent that, when contacted with the liquid reagent composition, changes the pH of the liquid reagent composition to 6.9 or higher.

In another aspect, the present disclosure provides an apparatus. The apparatus can comprise a container with an opening and a cuvette portion that is adapted to be operationally coupled to a luminometer, a liquid reagent composition comprising luciferin, and a sampling device having a sampling portion. The liquid reagent composition can be disposed in a closed compartment. The pH of the liquid reagent composition is about 6.8 or lower. The sampling portion is adapted to acquire and releasably retain a predetermined volume of a liquid sample in one or more cavity that is not substantially defined by space between fibers. The sampling portion of the device comprises a dry coating that includes an effective amount of a pH-adjusting reagent that, when contacted with the liquid reagent composition, changes the pH of the liquid reagent composition to 6.9 or higher.

In any embodiment of the above kit or apparatus, the pH-adjusting reagent can comprise a water-soluble reagent. In any of the above embodiments of the kit or the apparatus, the sampling portion can comprise a calibrated loop. In any of the above embodiments of the kit or the apparatus, the closed compartment can comprise a frangible wall. In some embodiments, the frangible wall can be disposed in the container between the opening and the cuvette portion. In some embodiments of the kit or the apparatus, the sampling device comprises the closed compartment, wherein the sampling device further comprises a structure that selectively releases the fluid composition from the container. In any of the above embodiments of the kit or the apparatus, the sampling portion can comprise a foam material. In any of the above embodiments of the kit or the apparatus, the pH-adjusting reagent can comprise a buffer component selected from the group consisting of N-[2-hydroxyethyl]piperazine-N'-[2-ethanesulfonic acid], N-[tris(hydroxymethyl)methyl] glycine, and combinations thereof. In any of the above embodiments of the kit or the apparatus, the pH-adjusting reagent can be coated in the one or more cavity. In any of the above embodiments of the kit or the apparatus, the coating further can comprise an effective amount of a cell extractant. In any of the above embodiments of the kit or the apparatus, the luciferase enzyme can consist essentially of a recombinant luciferase enzyme having luciferase activity that is less sensitive to variations in temperature, ionic detergents, and reducing agents than a corresponding non-recombinant luciferase enzyme. In any of the above embodiments of the kit or the apparatus, the coating optionally does not comprise an effective amount of a phosphate buffer component. In any of the above embodiments of the kit or the apparatus, the predetermined volume can be about 0.01 milliliters to about 0.25 milliliters.

In yet another aspect, the present disclosure provides a method. The method can comprise using a sampling device to obtain a predetermined volume of a liquid sample; contacting the predetermined volume of sample with a liquid reagent composition in a container to form a reaction mixture; and using a luminometer to detect light emitted from the reaction mixture. The sampling device comprises a sampling portion. The sampling portion is adapted to acquire and releasably retain a predetermined volume of liquid sample in one or more cavity. The one or more cavity is not substantially defined by space between a plurality of fibers. The sampling portion of the device comprises a dry coating that can include an effective amount of a pH-adjusting reagent that, when contacted with a liquid reagent composition having a pH of about 6.8 or lower, changes the pH of the liquid reagent composition to 6.9 or higher. The liquid reagent composition comprises a luciferin. The container comprises a cuvette portion adapted to be operationally coupled to the luminometer.

In any embodiment of the above method, the method further can comprise the step of agitating the predetermined volume of the sample and the liquid reagent composition in the container. In any of the above embodiments of the method, the liquid reagent composition further can comprise a luciferase enzyme. In any of the above embodiments of the method, wherein the luciferase enzyme activity can consist essentially of a recombinant luciferase enzyme having luciferase activity that is less sensitive to variations in temperature, ionic detergents, and reducing agents than a corresponding non-recombinant luciferase enzyme. In any of the above embodiments of the method, contacting the sampling device comprising the sample with liquid reagent composition can comprise contacting the sampling device with the liquid reagent composition at a temperature within a range of 10° C. and 35° C., inclusive. In any of the above embodiments of the method, after contacting the sampling device with liquid reagent composition, a substantially steady-state amount of light is emitted from the composition in less than 20 seconds.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a cell extractant can be interpreted to mean "one or more" cell extractants.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

FIG. 1 is a side view of one embodiment of a sampling device according to the present disclosure.

FIG. 1a is a detailed side view of the sampling portion of the sampling device of FIG. 1.

FIG. 2 is a side view of an alternative embodiment of a sampling device according to the present disclosure.

FIG. 3 is a side view of another alternative embodiment of a sampling device according to the present disclosure.

DETAILED DESCRIPTION

Figure 4:
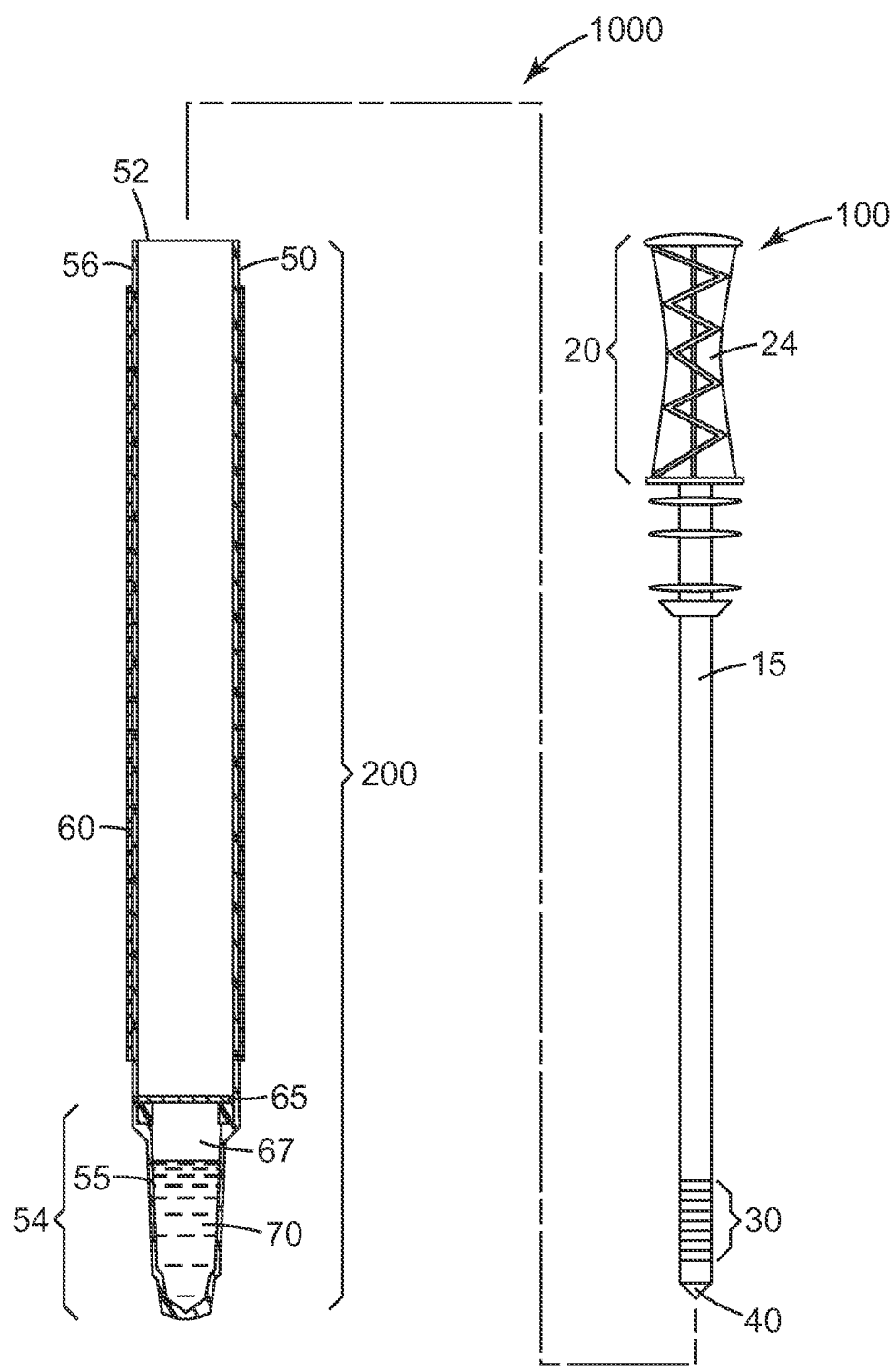
FIG. 4 is an exploded view, partially in section, of one embodiment of an apparatus according to the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to an apparatus and method for detecting ATP from organic residues and/or cells in a sample. According to the present disclosure, the ATP from cells is detected by contacting the sample with a cell extractant to release ATP and detecting the released ATP using an enzymatic reaction that involves the reaction of the released ATP with luciferase enzyme activity in the presence of luciferin and results in the production of measurable light.

In particular, the present disclosure provides an apparatus and/or a kit with a sampling device that is adapted such that it 1) can acquire and releasably retain a predetermined volume of liquid sample, 2) can use the liquid sample to rehydrate an effective amount of dry, rehydratable pH-adjusting reagent, and 3) can deliver the liquid sample and effective amount of pH-adjusting reagent into a container in order to facilitate a luciferase-catalyzed light-emitting reaction. Advantageously, the present disclosure provides kits and apparatuses that can be used to store aqueous mixtures comprising luciferin for extended periods of time and instantly to adjust the pH of the mixtures in order to reduce the lag time required for a glow-type luciferase enzyme activity to achieve stable light output (e.g., maximum light output) in the presence of ATP and luciferin, particularly at lower temperatures (e.g., temperatures below 20° C.

FIG. 1 shows one embodiment of a sampling device that can be used in an apparatus, kit and/or method according to the present disclosure. The sampling device 100 comprises a handling portion 20 and a sampling portion 30. In the illustrated embodiment, the sampling portion 30 is coupled to the handling portion 20 via an optional stem 15. Typically, the sampling device 100 is shaped and dimensioned to be received in a corresponding container (not shown). The handling portion 20 can be made from a variety of materials (e.g., wood, metal, plastic, glass) using processes known in the art and the handling portion 20 functions as a location at which the sampling device 100 can be grasped and/or manipulated during use. Optionally, the handling portion comprises a handle 24 that is shaped and/or textured to facilitate manual or mechanical gripping of the sampling device 100. Optionally, the sampling device 100 further can comprise a piercing tip 40.

The sampling portion 30 may include any suitable structure that defines at least one cavity capable of obtaining (via capillary pressure) and retaining a liquid sample from a sample source. In one embodiment, sampling portion 30 defines a single cavity. In other embodiments, the sampling portion 30 includes a plurality of cavities that that are not in fluidic communication. Regardless of whether sampling portion 30 comprises one or more cavity, the sampling portion 30 is designed to retain a predetermined maximum sample volume. The maximum sample volume may be selected, for example, based on the desired sensitivity of the test performed with the sample.

FIG. 1 shows one embodiment of a sampling portion 30 comprising a plurality of cavities 32. FIG. 1a shows a detailed view of the sampling portion 30 of FIG. 1. In the illustrated embodiment, the cavities 32 consist of indentations that circle the sampling device 100. A person having ordinary skill in the art will recognize the predetermined volume can be achieved using a variety of design configurations for the one or more cavity. For example, International Publication No. WO 2009/134509, which is incorporated herein by reference in its entirety, discloses a variety of sample acquisition devices comprising cavities that are suitable for obtaining and retaining a predetermined volume of liquid sample.

In an alternative embodiment, the sampling portion of a sampling device of the present disclosure may comprise a plurality of cavities formed in a foam material. Foam articles (e.g., sponges, sponges mounted on a handle) for obtaining samples from environmental surfaces are known in the art. FIG. 2 shows a sampling device 100' comprising a sampling portion 30 that comprises a foam material. The foam material comprises individual cells or void spaces that are capable of obtaining and retaining a liquid sample. Suitable foam materials for use in a sampling device of the present disclosure include, for example, polyurethane foams, polyethylene foams, and polystyrene foams. In some embodiments, the foams may be treated (e.g., corona-treated or electron beam-treated) in order to make the surface of the polymer more hydrophilic. The foam material can be coupled to a stem 15 and/or a handling portion 20 using materials (e.g., adhesives, mechanical fasteners, or the like) and processes known in the art.

FIG. 3 shows yet another alternative embodiment of a sampling device 100" according to the present disclosure. In this embodiment, the sampling portion 30 comprises a calibrated loop 34 configured to obtain and retain a predetermined volume of sample liquid. Calibrated loops are known in the art and the loop may take a variety of forms including, for example, a circular form (as shown in FIG. 3) or an obround form. Optionally, any sampling device according to the present disclosure further may comprise a coating area on which a coating comprising a pH-adjusting reagent according to the present disclosure can be disposed. An embodiment of a sampling device 100" comprising a coating area 36 onto which a coating can be applied is shown in FIG. 3. The coating can be comprise an effective amount of a pH-adjusting reagent that, when contacted (e.g., mixed) with a liquid reagent composition according to the present disclosure, adjusts the pH of the liquid reagent composition having an initial pH of 6.8 or lower to an adjusted pH of 6.9 or higher, preferably to an adjusted pH of about pH 7.2-8.0, more preferably to an adjusted pH of about pH 7.2-7.8. Also shown in FIG. 3 are the handling portion 20 comprising a handle 24, the stem 15, and piercing tip 40. In any embodiment, the pH-adjusting reagent can be a water-soluble reagent.

In some embodiments, sampling portion 30 is formed of a material having a surface energy in a range of about 20 dynes/centimeter (dyn/cm) to about 82 dyn/cm, such as about 45 dyn/cm to about 72 dyn/cm. In some embodiments, the material for sampling portion 30 is selected to have a surface energy close to that of water, or about 72 dyn/cm. A sample may be easier to remove from sampling portion 30 compared to a conventional medical swab that includes a fibrous tip because the sample is held within sampling portion 30 by surface energy, rather than absorption, as is the case with some conventional medical swabs. That is, less energy may be required to remove sample liquid and/or liquid-suspended particles from sampling portion 30. In some cases, a large percentage of sample particles are removed from sampling portion 30 without the aid of a machine vortexer, although a machine vortexer may be utilized to help elute the sample from sampling portion 30.

In general, sampling portion 30 is comprised of a material that achieves the desired sample acquisition characteristics, which may depend upon the type of sample acquired (e.g., some liquid samples may include dissolved or suspended solids that affect the surface tension of the liquid). Material properties that may affect the ability of sampling portion 30 to acquire and retain a sample include, for example, surface energy. For example, as described above, the material may be selected to have a particular surface energy in order to draw the sample into the one or more cavity defined by sampling portion 30 by capillary force. Other characteristics of the material from which the sampling portion is made may include substantial inertness relative to the sample or a relatively low rate of elution of chemicals or other contaminants that may affect luciferase enzyme activity, e.g., when the sample is released from sampling portion 30.

In some embodiments, sampling portion 30 may include a base material that does not necessarily include the desired sample acquisition characteristics, and an external layer (e.g., a coating) comprising a material that affords hydrophilic, hydrophobic, positively-charged or negatively-charged surfaces to achieve the desired sample acquisition characteristics. For example, an inorganic coating (e.g., a silica coating) or an organic coating (e.g., polymeric coatings, such as polyacrylate) may afford hydrophilic characteristics to sampling portion 30. Surface energy (or surface tension) characteristics of a material forming sampling portion 30 may also be achieved with the aid of physical treatments, such as, but not limited to, corona treating in which the material being treated is exposed to an electrical discharge, or corona, electron beam treatments.

In some embodiments, the sampling portion 30 may be formed at least in part of relatively rigid polymer (e.g., nylon, polysulfone, polycarbonate, or combinations thereof) or it may be formed using a more compliant polymer, such as silicone. Example materials for sampling portion 30 include, but are not limited to, any thermoplastic materials suitable for casting, profile extrusion, molding (e.g., injection molding) or embossing including, for example, polyolefins, polyesters, polyamides, poly(vinyl chloride), polymethyl methacrylate, polycarbonate, nylon, and the like. In other embodiments, sampling portion 30 may be formed by molding or embossing a sheet of suitable material into the desired cavity structure.

A sampling device of the present disclosure comprises a dry coating. In any embodiment, the dry coating can be disposed on and/or in (e.g., in a cavity) the sampling portion of the device so that, when the device is dipped into the liquid sample, the coating is contacted with the liquid sample. In any embodiment, at least a part of the dry coating can be disposed on another portion (e.g., the stem, the piercing tip) of the sampling device. The dry coating includes an effective amount of a pH-adjusting reagent that, when contacted (e.g. mixed) with a liquid reagent composition of the present disclosure, changes the pH of the liquid reagent composition. In any embodiment, the pH-adjusting reagent comprises a water-soluble reagent. In any embodiment, the pH-adjusting reagent comprises a component of a buffer solution (e.g. the pH-adjusting reagent comprises a base or a conjugate acid) having a pKa of 7.0 or higher, preferably having a pKa of 7.2 or higher. pH-adjusting reagents that each comprise a suitable buffer component include, but are not limited to, N-[2-hydroxyethyl]piperazine-N'-[2-ethanesulfonic acid], N-[tris(hydroxymethyl) methyl]glycine, and combinations thereof. In some embodiments, the coating does not comprise an effective amount of a pH-adjusting reagent comprising phosphate. A pH-adjusting reagent comprising an amount of phosphate effective to change the pH of the liquid reagent composition from an initial pH 6.8 or lower to an adjusted pH of 6.9 or higher may also be sufficient to at least partially inhibit luciferase enzyme activity. In any embodiment, the pH-adjusting reagent comprises a metallic base (e.g., sodium hydroxide, potassium hydroxide).

In any embodiment, the coating further can comprise a cell lysis agent that does not substantially inhibit luciferase enzyme activity. Examples of suitable cell lysis agents include, but are not limited to, chlorhexidine digluconate, TRITON™ X100, lysozyme, lysostaphin, bacteriophage lysin, a quaternary ammonium compound (e.g., benzalkonium chloride, benzethonium chloride), cetyl trimethylammonium chloride (CTAB), dodecyltrimethylammonium chloride (DTAB), TWEEN 20, TWEEN 80, and a combination of any two or more of the foregoing.

The amount of pH-adjusting reagent coated onto the sampling device should be enough to change the pH of the liquid reagent composition from an initial (i.e., before contact with the pH-adjusting reagent) pH of 6.8 or lower to an adjusted pH of about 6.9 or higher (after contact with the pH-adjusting reagent). Preferably, the amount of pH-adjusting reagent coated on the sampling device should be enough to change the pH of the liquid reagent composition from an initial pH of 6.8 or lower to a pH about 7.2 or higher.

The coating can be applied to the sampling device using any suitable coating method. In any embodiment, the coating initially can be applied to the sampling device as a liquid coating (i.e., the pH-adjusting reagent is dissolved or suspended in a solvent such as water, for example). The solvent is subsequently dried to leave the substantially dry pH-adjusting reagent coated on the sampling device. In any embodiment, the liquid coating is applied by dipping the sampling device (e.g., the sampling portion of the sampling device) into a liquid comprising the pH-adjusting reagent. While immersed in the coating liquid, the sampling device can be agitated to facilitate movement of the coating liquid into the one or more cavity of the sampling portion. After coating the device, the coated portion can be dried (e.g., in a stream of air, a convection oven, or the like) under conditions (e.g., ambient or above-ambient (warm) temperatures) sufficient to evaporate the solvent without substantially degrading the pH-adjusting reagent and/or cell lysis agent.

Kits and apparatuses of the present disclosure further comprise a container. The container functions as a vessel in which to contact a sample with the liquid reagent composition described herein. The container comprises an opening and is configured (e.g., shaped and dimensioned) to receive at least a portion (e.g., the sampling portion) of the sampling device. FIG. 4 shows an exploded view, partially in section, of one embodiment of an apparatus comprising a container according to the present disclosure. The apparatus 1000 comprises a sampling device 100 comprising a handling portion 20 with a handle 24 and a sampling portion 30 according to any of the embodiments described herein. The apparatus 1000 further comprises a container 200, shown in cross-section in FIG. 4.

The container comprises at least one wall 50 and an opening 52, the opening configured to receive the sampling device 100. As discussed below, the apparatus 1000 with the opening 52 shown in the illustrated embodiment of FIG. 4 is shaped and dimensioned to receive the entire sampling device 100. The container further comprises a cuvette portion 54 that is adapted to be operationally coupled to a luminometer. Typically, the cuvette portion 54 is operationally coupled to a luminometer by placing the cuvette portion 54 of the container 200, or the entire container 200, into a complementary-shaped receiving compartment of the luminometer. The cuvette portion 54 is fabricated from optically-transmissible material (e.g., glass or a polymeric material such as poyethylene, polypropylene, polycarbonate, or polystyrene, for example) that permits the transmission there through of light emitted as a product of a reaction catalyzed by luciferase enzyme.

The container 200 may be fabricated as a unitary article (not shown), for example, using extrusion and/or molding processes known in the art. Alternatively, portions of the container 200, such as the cylindrically-shaped sleeve 56 and the cuvette 55 of the illustrated embodiment of FIG. 4, may be fabricated separately and coupled together using suitable means (e.g., an adhesive, a heat sealing process, a sonic weld, and/or by press-fitting the sleeve 56 and cuvette 55 together). The sleeve 56 may be fabricated via a molding or extrusion process, for example, using a plastic polymer such as polypropylene or polyethylene, for example. The cuvette 55 can be formed in a variety of geometric shapes, such as cubic, cuboid, cylindrical, conical, frusto-conical, other suitable geometric shapes, and combinations thereof. Preferably, the walls of the cuvette 55 are configured to allow the passage of light (e.g., visible light) into and/or out of the cuvette 55. Optionally, the container further may comprise a lamina 60. The lamina 60 can hold the cuvette 55 firmly together with the sleeve 56. The lamina 60 can be made from paper or a plastic film, for example, and may be used as a label.

Figure 5:
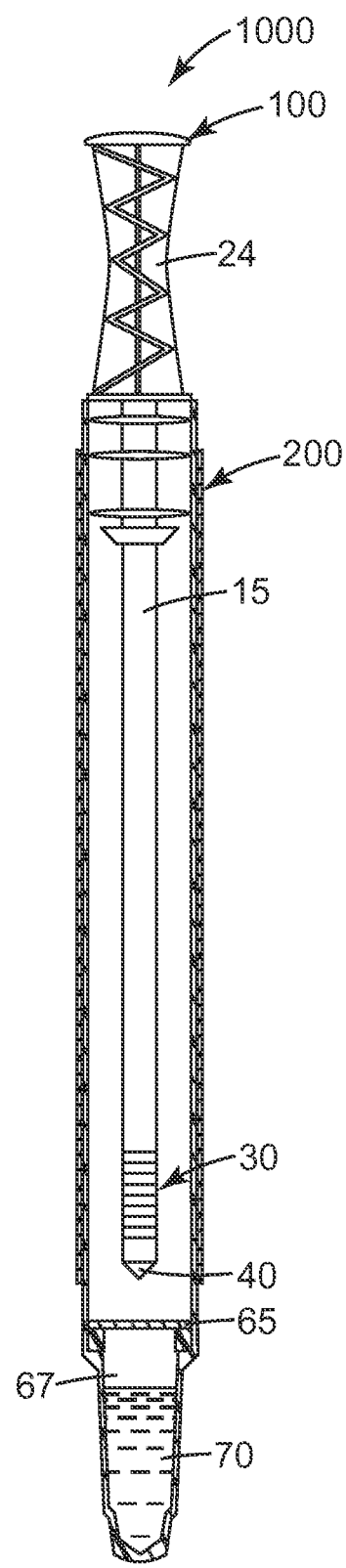
FIG. 5 is a side view, partially in section, of the assembled apparatus of FIG. 4 showing the sampling device and the container in a first operational position with respect to each other.
Figure 6:
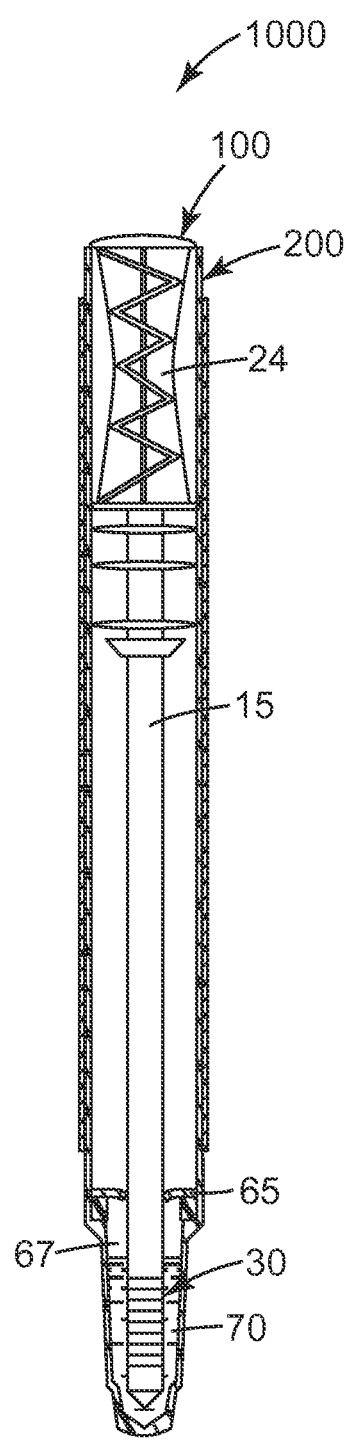
FIG. 6 is a side view, partially in section, of the assembled apparatus of FIG. 4 showing the sampling device and the container in a second operational position with respect to each other.

Kits and apparatuses of the present disclosure further comprise a liquid reagent composition (liquid reagent composition 70 shown in FIGS. 4-6). The liquid reagent composition comprises luciferin at a concentration (e.g., 0.3-0.4 mg/L luciferin) sufficient to facilitate a light-emitting reaction in the presence of luciferase; preferably, a glow-type luciferase; and a source of ATP. In a method of the present disclosure, the source of ATP can be a sample as disclosed herein or a solution containing a predefined amount or concentration of ATP (i.e., a positive control or an ATP standard). In any embodiment, the liquid reagent composition can comprise an aqueous solution. The liquid reagent composition used in the apparatus or kit of the present disclosure has an initial (i.e., before contact with the pH-adjusting reagent) pH of 6.8 or lower. Preferably, liquid reagent composition has an initial (i.e., before contact with the pH-adjusting reagent) pH of 6.4 or lower.

In any embodiment, the liquid reagent composition optionally may comprise a buffering agent. Suitable buffering agents have a pKa that is effective to maintain the pH of the liquid reagent composition at a pH of 6.8 or lower, preferably at a pH of 6.4 or lower. N-(2-acetamido)-iminodiacetic acid (ADA) is a nonlimiting example of a suitable buffering agent. The buffering agent should be present in the liquid reagent composition in an amount (e.g., about 16 mM ADA in 425 microliters of liquid reagent composition at pH 6.4-6.8) that is high enough to effectively maintain the pH of the liquid reagent composition, yet low enough so that it does not substantially resist a change in the pH of the liquid reagent composition mediated by the pH-adjusting reagent coated on the sampling portion of the sampling device. In any embodiment, the liquid reagent composition further may comprise a luciferase enzyme. In any embodiment, the luciferase enzyme can consist essentially of a recombinant luciferase enzyme having luciferase activity that is less sensitive to variations in temperature, ionic detergents, and reducing agents than a corresponding non-recombinant luciferase enzyme. The luciferase enzyme can be present in the liquid reagent composition at a concentration of about 9 mg/L, for example. In any embodiment, the liquid reagent composition further can comprise a source of magnesium ions (e.g., magnesium diacetate tetrahydrate). The source of magnesium ions can be present at a concentration (e.g., about 3 mM, for example) that does not substantially interfere with luciferase enzyme activity when the liquid reagent composition is mixed with the liquid sample. In any embodiment, the liquid reagent composition further can comprise a protein (e.g., bovine serum albumin) Without being bound by theory, the protein may stabilize the luciferase enzyme during prolonged storage and/or make the luciferase enzyme less susceptible to protease enzyme activities. At its working concentration, the protein should not substantially interfere with luciferase enzyme activity when the liquid reagent composition is mixed with the liquid sample. The protein may be present in the liquid reagent composition at a concentration of about 0.046 weight percent, for example. In any embodiment, the liquid reagent composition further can comprise a preservative (e.g., 0.046 weight percent sodium azide) at a concentration that does not substantially interfere with luciferase enzyme activity when the liquid reagent composition is mixed with the liquid sample. In any embodiment, the liquid reagent composition further may comprise ethylenediamine tetraacetic acid (EDTA). Without being bound by theory, the EDTA can act as a preservative in the liquid reagent composition and may also function to chelate ions present in the liquid reagent composition and/or the liquid sample.

In any embodiment, the liquid reagent composition can be disposed in a closed compartment. In some embodiments, the closed compartment comprises a frangible wall. In the illustrated embodiment of FIG. 4, the container further comprises a liquid-resistant frangible wall 65 disposed proximate the cuvette 55 that forms a compartment 67. The frangible wall 65 can be made from a water-resistant material, such as plastic film, metal foil, or a metal-coated plastic film, for example. The frangible wall 65 can be coupled to the cuvette 55 and/or the sleeve 56 via an adhesive, a heat seal, a sonic weld, or other means known in the art to form a liquid-resistant seal to retain the liquid reagent composition 70 in the compartment 67.

In an alternative embodiment (not shown), the liquid reagent composition may be disposed in a frangible ampoule (e.g., a glass or polymeric ampoule) which is disposed in the container. The liquid reagent composition can be released from the frangible ampoule by squeezing the container with enough force to fracture the ampoule or by urging the sampling device (e.g., the piercing tip of the sampling device) against the ampoule with enough force to fracture the ampoule.

In a further embodiment (not shown), the liquid reagent composition may be disposed in a compartment disposed in the sampling device. Nason (U.S. Pat. No. 5,266,266, which is incorporated herein by reference in its entirety) discloses a swab device comprising a hollow stem and a liquid-containing closed compartment with an actuatable valve (break-off nib) that releases the liquid into the hollow stem for delivery into tube in which at least a portion of the swab is disposed. Any sampling device of the present disclosure may be modified to include the hollow stem and reagent chamber of Nason. The reagent chamber can contain the liquid reagent composition of the present disclosure and the liquid reagent composition can be transferred into the container of the present disclosure using the technique described by Nason. The liquid reagent composition can be transferred to the container before or after the liquid sample is acquired using the sampling device according to the present disclosure. Other compartments for temporarily storing liquid reagent compositions to be used in a reaction (e.g., a chemical and/or enzymatic reaction) are known in the art and a person of ordinary skill in the art will recognize such compartments can be used to temporarily contain the liquid reagent composition of the present disclosure. Non-limiting examples of such compartments can be found in U.S. Pat. Nos. 7,399,984; 6,548,018; 5,965,453; and 6,524,530, which are all incorporated herein by reference in their entirety.

The present disclosure provides a kit. The kit may be used, for example, to detect a presence or absence of ATP in a liquid sample according the method described herein. In any embodiment, the kit may comprise instructions disclosing an embodiment of the method disclosed herein.

Kits of the present disclosure comprise a container according to any of the embodiments disclosed herein. The container comprises an opening and a cuvette portion that is adapted to be operationally coupled to a luminometer. Kits of the present disclosure further comprise a liquid reagent composition comprising luciferin according to any of the embodiments disclosed herein. The initial pH (i.e., before contact with a pH-adjusting reagent of the present disclosure) of the liquid reagent composition is about pH 6.8 or lower; preferably, about pH 6.4 or lower. Kits of the present disclosure further comprise a sampling device having a sampling portion and a handling portion according to any of the embodiments disclosed herein. The liquid reagent composition is disposed in a closed compartment disposed in the container or the sampling device, as disclosed herein. The sampling portion of the sampling device is adapted to acquire and releasably retain a predetermined volume of a liquid sample, as described herein, in one or more cavity that is not substantially defined by space between a plurality of fibers. The sampling portion of the sampling device comprises a dry coating that includes an effective amount of a pH-adjusting reagent that, when contacted (e.g., mixed) with the liquid reagent composition, changes the pH of the liquid reagent composition to 6.9 or higher, preferably to about pH 7.2-8.0, more preferably to about pH 7.2-7.8. In any embodiment, the pH-adjusting reagent comprises a water-soluble reagent.

Kits and apparatuses of the present disclosure can be used in a method of detecting a presence or an absence of ATP in a liquid sample. The presence of ATP in a sample can indicate a possible presence of organic residues and/or microorganisms (e.g., pathogenic microorganisms) in the sample. Moreover, the quantity of ATP in the sample can be an indicator of the relative number of microorganisms in the sample. Therefore, it is desirable to test a predetermined volume of sample, so that the amount of ATP per unit volume of sample can be determined. The amount of ATP per unit volume of sample can be compared to a predetermined value to determine whether the sample is acceptable for use in a particular application (e.g., food or beverage production), whether a cleaning process has been effective in removing organic residues, and/or whether a biocide treatment has been effective in reducing the number of microorganisms.

In one embodiment, the method comprises using a sampling device to obtain a predetermined volume of liquid sample, contacting the predetermined volume of sample with a liquid reagent composition in a container to form a reaction mixture, and using a luminometer to detect light emitted from the reaction mixture. The predetermined volume of liquid sample can be about 10 microliters to about 250 microliters. In some embodiments, the predetermined volume of liquid sample can be about 100 microliters to about 200 microliters. In some embodiments, the predetermined volume of liquid sample can be about 125 microliters to about 175 microliters.

The sample comprises a liquid. The liquid may comprise water. The sample further may comprise solids that are dissolved, dispersed, and/or suspended in the liquid. Non-limiting examples of suitable samples include clean-in-place (CIP) rinse-water samples, process and cooling water samples, and endoscope rinse water samples.

The sampling device used in the method of the present disclosure can be any sampling device disclosed herein. The sampling device comprises a sampling portion and a handling portion. The sampling portion is adapted to acquire and releasably retain a predetermined volume of liquid sample in one or more cavity. The one or more cavity is not substantially defined by space between a plurality of fibers. The sampling portion of the device comprises a dry coating that includes an effective amount of a pH-adjusting reagent that, when contacted (e.g., mixed) with a liquid reagent composition having an initial pH of 6.8 or lower, adjusts the pH of the liquid reagent composition to 6.9 or higher.

The liquid reagent composition used in the method of the present disclosure comprises a luciferin (e.g., firefly luciferin). Luciferin is a compound that undergoes oxidation by luciferase enzyme activity to produce oxyluciferin and light. Luciferin compounds can be unstable when stored for extended periods of time in liquid solutions at a pH above 6.8. Thus, the liquid reagent composition used in the method of the present disclosure has an initial pH of 6.8 or lower. Preferably, liquid reagent composition has an initial pH of 6.4 or lower.

In any embodiment, the liquid reagent composition may further comprise a luciferase enzyme. In a preferred embodiment, the luciferase enzyme comprises a recombinant luciferase enzyme having luciferase activity that is less sensitive than a corresponding non-recombinant luciferase enzyme to variations in temperature, ionic detergents, and reducing agents. In some embodiments, the luciferase enzyme consists essentially of a recombinant luciferase enzyme having luciferase activity that is less sensitive to variations in temperature, ionic detergents, and reducing agents than a corresponding non-recombinant luciferase enzyme.

In any embodiment, the liquid reagent composition optionally may comprise a buffering agent. The buffering agent can be used to maintain the liquid reagent composition at a pH (e.g., ≤6.8) that is suitable to store a liquid solution containing luciferin. N-(2-acetamido)-iminodiacetic acid (ADA) is a nonlimiting example of a suitable buffering agent. The buffering agent should be present in the liquid reagent composition in an amount (e.g., about 16 mM ADA in 425 microliters of liquid reagent composition at pH 6.4-6.8) that is high enough to effectively maintain the pH of the liquid reagent composition, yet low enough so that it does not substantially resist a change in the pH of the liquid reagent composition mediated by the pH-adjusting reagent coated on the sampling portion of the sampling device.

The container used in the method of the present disclosure comprises a cuvette portion. The cuvette portion permits the transmission there through of light emitted as a product of the reaction catalyzed by luciferase enzyme. The cuvette portion is adapted (e.g., shaped and dimensioned) to be operationally coupled to the luminometer. In some embodiments, using a luminometer to detect light emitted from the reaction mixture comprises detecting a presence or an absence of ATP in the liquid sample. In some embodiments, using a luminometer to detect light emitted from the reaction mixture comprises measuring a quantity (e.g., a relative quantity or an absolute quantity) of ATP present in the liquid sample.

Contacting the predetermined volume of sample with a liquid reagent composition in a container to form a reaction mixture comprises bringing the sampling portion of the sampling device into contact with the liquid reagent composition in a container. The contact may be achieved, for example, by immersing at least a part; preferably, the entire sampling portion; of the sampling device in the liquid reagent composition. The contact forms a reaction mixture (e.g., by diffusion of at least part of the liquid sample into the liquid reagent composition). If it is not already present in the liquid reagent composition, luciferase can be added to the reaction mixture. Thus, if ATP is present in the liquid sample, the ATP can facilitate a light-emitting reaction catalyzed by luciferase enzyme. The light-emitting reaction can be detected in the aforementioned luminometer.

FIGS. 5 and 6 illustrate one embodiment of a process of contacting a predetermined volume of sample with a liquid reagent composition in a container to form a reaction mixture. After obtaining the predetermined volume of liquid sample using the sampling device 100, the sampling device is inserted into the container 200. FIG. 5 shows the sampling device 100 with the stem 15 and sampling portion 30 in the container. In this configuration, the sampling device 100 and container 200 are disposed in a first operational position with respect to one another and the apparatus 1000 is ready to bring the liquid sample into contact with the liquid reagent composition 70 located in the compartment 67. Using manual or mechanical pressure against the handle 24 of the sampling device 100, the piercing tip 40 is urged toward the compartment 67 until it pierces the frangible wall 65 and brings the liquid sample (not shown) associated with the sampling portion 30 into contact with the liquid reagent composition 70, as shown in FIG. 6. In the illustrated embodiment of FIG. 6, the sampling device 100 and container 200 are disposed in a second operational position with respect to each other. In this embodiment, the sampling device 100 is fully-inserted into the container 200 and the sampling portion 30 of the sampling device is contacting the liquid reagent composition 70.

In any embodiment, contacting the predetermined volume of sample with a liquid reagent composition in a container to form a reaction mixture further can comprise the step of agitating the sample and the liquid reagent composition in the container. This may be done manually or mechanically, for example, by rapidly shaking the container in a swirling motion, a pendulum-like motion, or by contacting the container with a machine that vibrates the container.

The cuvette portion of the container is operationally coupled to the luminometer in order to detect the light emission resulting from luciferase enzyme activity. Commercially-available luminometers are suitable for use in any embodiment of the method of the present disclosure. A non-limiting example of a suitable luminometer is the 3M™ CLEAN-TRACE™ NG Luminometer commercially available from 3M Company, St. Paul, Minn. Typically, the cuvette is operationally coupled by placing a portion (e.g., the cuvette portion) of the container or the entire container into a corresponding receiving compartment of the luminometer. The cuvette portion may be operationally coupled to the luminometer before or after forming the reaction mixture. Typically, the cuvette portion is operationally coupled to the luminometer after the reaction mix is formed. In some embodiments the cuvette portion is operationally coupled to the luminometer up to 5 seconds after forming the reaction mixture. In some embodiments the cuvette portion is operationally coupled to the luminometer up to 10 seconds after forming the reaction mixture. In some embodiments the cuvette portion is operationally coupled to the luminometer up to 15 seconds after forming the reaction mixture. In some embodiments the cuvette portion is operationally coupled to the luminometer up to 20 seconds after forming the reaction mixture. In some embodiments the cuvette portion is operationally coupled to the luminometer up to 30 seconds after forming the reaction mixture. In some embodiments the cuvette portion is operationally coupled to the luminometer up to 45 seconds after forming the reaction mixture. In some embodiments the cuvette portion is operationally coupled to the luminometer up to 60 seconds after forming the reaction mixture. In some embodiments the cuvette portion is operationally coupled to the luminometer up to 90 seconds after forming the reaction mixture. In some embodiments the cuvette portion is operationally coupled to the luminometer up to 2 minutes after forming the reaction mixture. Preferably, the cuvette is operationally coupled to the luminometer within about 5 to 10 seconds after forming the reaction mixture.

After operationally coupling the cuvette portion to the luminometer, the light-emission is monitored by the luminometer. After the reaction mixture is formed, it may take a period of time for the reaction to reach a relatively stable quantity of light emission. This phenomenon is illustrated by the data in Tables 4-9. The length of time for the light emission to reach a relatively stable plateau is inversely related to the temperature of the reaction, as summarized in Table 11.

In any embodiment of the method, the liquid reagent composition comprises luciferin at a concentration (e.g., about 0.3-0.4 mg/L luciferin) sufficient to facilitate a light-emitting reaction in the presence of luciferase and a source of ATP. In the method of the present disclosure, the source of ATP can be a liquid sample as disclosed herein or a solution containing a predefined amount or concentration of ATP (i.e., a positive control or an ATP standard). In any embodiment, the liquid reagent composition can comprise an aqueous solution. The liquid reagent composition used in the apparatus or kit of the present disclosure has an initial pH (i.e., before contact with a pH-adjusting reagent of the present disclosure) of 6.8 or lower. Preferably, liquid reagent composition has an initial pH of 6.4 or lower.

In any embodiment of the method, the liquid reagent composition optionally may comprise a buffering agent. Suitable buffering agents have a pKa that is effective to maintain the initial pH of the liquid reagent composition at a pH of 6.8 or lower, preferably at a pH of 6.4 or lower. N-(2-acetamido)-iminodiacetic acid (ADA) is a nonlimiting example of a suitable buffering agent. The buffering agent should be present in the liquid reagent composition in an amount (e.g., about 16 mM ADA in 425 microliters of liquid reagent composition at pH 6.4-6.8) that is high enough to effectively maintain the pH of the liquid reagent composition, yet low enough so that it does not substantially resist a change in the pH of the liquid reagent composition mediated by the pH-adjusting reagent coated on the sampling portion of the sampling device. In any embodiment of the method, the liquid reagent composition further may comprise a luciferase enzyme. In any embodiment of the method, the luciferase enzyme can consist essentially of a recombinant luciferase enzyme having luciferase activity that is less sensitive to variations in temperature, ionic detergents, and reducing agents than a corresponding non-recombinant luciferase enzyme. The luciferase enzyme can be present in the liquid reagent composition at a concentration of about 9 mg/L, for example. In any embodiment of the method, the liquid reagent composition further can comprise a source of magnesium ions (e.g., magnesium diacetate tetrahydrate). The source of magnesium ions can be present at a concentration (e.g., about 3 mM, for example) that does not substantially interfere with luciferase enzyme activity when the liquid reagent composition is mixed with the liquid sample. In any embodiment of the method, the liquid reagent composition further can comprise a protein (e.g., bovine serum albumin). The protein may be present in the liquid reagent composition at a concentration of about 0.046 weight percent, for example. In any embodiment of the method, the liquid reagent composition further can comprise a preservative (e.g., 0.046 weight percent sodium azide) at a concentration that does not substantially interfere with luciferase enzyme activity when the liquid reagent composition is mixed with the liquid sample.

In any embodiment of the method of the present disclosure, contacting the sampling device comprising the liquid sample with liquid reagent composition comprises contacting the sampling device with the liquid reagent composition at a particular temperature (e.g. ambient temperature). In general, when the contact occurs at lower temperatures, a longer period of time is required for the light-emitting reaction to reach a relatively stable amount of light emission. Conversely, when the contact occurs at higher temperatures, a shorter period of time is required for the light-emitting reaction to reach a relatively stable amount of light emission. In any embodiment of the method of the present disclosure, contacting the sampling device comprising the liquid sample with liquid reagent composition comprises contacting the liquid sample with the liquid reagent composition at temperature within a range of 10° C. and 35° C., inclusive. Preferably, contacting the sampling device comprising the liquid sample with liquid reagent composition comprises contacting the liquid sample with the liquid reagent composition at temperature within a range of 15° C. and 30° C., inclusive.

In any embodiment of the method, after contacting the sampling device with the liquid reagent composition, a substantially steady-state amount of light is emitted from the composition after a period of time. As discussed above, the period of time may be affected by the temperature at which the contact occurs. In any embodiment of the present disclosure, a substantially steady-state amount of light is emitted from the composition in less than 25 seconds (e.g., when contact occurs at a temperature of about 10° C. to about 20° C.). In any embodiment of the present disclosure, a substantially steady-state amount of light is emitted from the composition in about 22 seconds or less (e.g., when contact occurs at a temperature of about 10° C. to about 20° C.). In some embodiments, a substantially steady-state amount of light is emitted from the composition in less than 20 seconds (e.g., when contact occurs at a temperature of about 14° C. to about 20° C.). In some embodiments, a substantially steady-state amount of light is emitted from the composition in about 10 seconds or less (e.g., when contact occurs at a temperature of about 20° C.).

The method of the present invention substantially reduces the amount of time necessary for a luciferase enzyme, in contact with a sample comprising ATP and a liquid reagent composition according to the present disclosure, to catalyze a light-emitting reaction that is substantially steady state. Table 11 (below) shows the mean amount of time required for the reaction to reach a substantially steady-state light emission is reduced about 3-fold by the method of the present disclosure at temperatures between 10° C. and 20° C., inclusive.

Embodiments

Embodiment A is a kit, comprising:
a container with an opening and a cuvette portion that is adapted to be operationally coupled to a luminometer;
a liquid reagent composition comprising luciferin, wherein the liquid reagent composition is disposed in a closed compartment, wherein the pH of the liquid reagent composition is about 6.8 or lower; and
a sampling device having a sampling portion and a handling portion;
wherein the sampling portion is adapted to acquire and releasably retain a predetermined volume of a liquid sample in one or more cavity that is not substantially defined by space between a plurality of fibers;
wherein the sampling portion of the sampling device comprises a dry coating that includes an effective amount of a pH-adjusting reagent that, when contacted with the liquid reagent composition, changes the pH of the liquid reagent composition to 6.9 or higher.

Embodiment B is an apparatus, comprising:
a container with an opening and a cuvette portion that is adapted to be operationally coupled to a luminometer;
a liquid reagent composition comprising luciferin, wherein the liquid reagent composition is disposed in a closed compartment, wherein the pH of the liquid reagent composition is about 6.8 or lower; and
a sampling device having a sampling portion and a handling portion;
wherein the sampling portion is adapted to acquire and releasably retain a predetermined volume of a liquid sample in one or more cavity that is not substantially defined by space between a plurality of fibers;
wherein the sampling device comprises a dry coating that includes an effective amount of a pH-adjusting reagent that, when contacted with the liquid reagent composition, adjusts the pH of the liquid reagent composition to 6.9 or higher.

Embodiment C is the kit of Embodiment A or the apparatus of Embodiment B, wherein the dry coating is disposed on the sampling portion of the sampling device.

Embodiment D is the kit or the apparatus of any one of the preceding Embodiments, wherein the pH-adjusting reagent comprises a water-soluble reagent.

Embodiment E is the kit or the apparatus of any one of the preceding Embodiments, wherein the sampling portion comprises a calibrated loop.

Embodiment F is the kit or the apparatus of any one of the preceding Embodiments, wherein the closed compartment comprises a frangible wall.

Embodiment G is the kit or the apparatus of Embodiment F, wherein the frangible wall is disposed in the container between the opening and the cuvette portion.

Embodiment H is the kit of Embodiment A or the apparatus of Embodiment B, wherein the sampling device comprises the closed compartment, wherein the sampling device further comprises a structure that selectively releases the fluid composition from the container.

Embodiment I is the kit or the apparatus of any one of the preceding Embodiments, wherein the sampling portion comprises a foam material.

Embodiment J is the kit or the apparatus of any one of the preceding Embodiments, wherein the pH-adjusting reagent comprises a buffer component selected from the group consisting of N-[2-hydroxyethyl]piperazine-N'-[2-ethanesulfonic acid], N-[tris(hydroxymethyl)methyl]glycine, and combinations thereof.

Embodiment K is the kit or the apparatus of any one of the preceding Embodiments, wherein the pH-adjusting reagent is coated in the one or more cavity.

Embodiment L is the kit or the apparatus of any one of the preceding Embodiment, wherein the coating further comprises an effective amount of a cell extractant.

Embodiment M is the kit or the apparatus of any one of the preceding Embodiments, wherein the luciferase enzyme consists essentially of a recombinant luciferase enzyme having luciferase activity that is less sensitive to variations in temperature, ionic detergents, and reducing agents than a corresponding non-recombinant luciferase enzyme.

Embodiment N is the kit or the apparatus of any one of the preceding Embodiments, wherein the coating does not comprise an effective amount of a phosphate buffer component.

Embodiment O is the kit or the apparatus of any one of the preceding Embodiments, wherein the predetermined volume is about 0.01 milliliters to about 0.25 milliliters.

Embodiment P is a method, comprising:
using a sampling device to obtain a predetermined volume of a liquid sample;
  wherein the sampling device comprises a sampling portion and a handling portion;
  wherein the sampling portion is adapted to acquire and releasably retain a predetermined volume of liquid sample in one or more cavity, wherein the one or more cavity is not substantially defined by space between a plurality of fibers;
  wherein the sampling device comprises a dry coating that includes an effective amount of a pH-adjusting reagent that, when contacted with a liquid reagent composition having a pH of about 6.8 or lower, changes the pH of the liquid reagent composition to 6.9 or higher;
    wherein the liquid reagent composition comprises a luciferin;
contacting the predetermined volume of sample and the pH-adjusting reagent with a liquid reagent composition in a container to form a reaction mixture; and
using a luminometer to detect light emitted from the reaction mixture;
  wherein the container comprises a cuvette portion adapted to be operationally coupled to the luminometer.

Embodiment Q is the method of Embodiment P, further comprising the step of agitating the predetermined volume of the sample and the liquid reagent composition in the container.

Embodiment R is the method of Embodiment P or Embodiment Q, wherein the liquid reagent composition further comprises a luciferase enzyme.

Embodiment S is the method of Embodiment R, wherein the luciferase enzyme activity consists essentially of a recombinant luciferase enzyme having luciferase activity that is less sensitive to variations in temperature, ionic detergents, and reducing agents than a corresponding non-recombinant luciferase enzyme.

Embodiment T is the method of any one of Embodiments P through S, wherein contacting the sampling device comprising the sample with liquid reagent composition comprises contacting the sampling device with the liquid reagent composition at a temperature within a range of 10° C. and 35° C., inclusive.

Embodiment U is the method of any one of Embodiments P though T wherein, after contacting the sampling device with liquid reagent composition, a substantially steady-state amount of light is emitted from the composition in less than 20 seconds.

Objects and advantages of this invention are further illustrated by the following examples, but the particular materials and amounts thereof recited in these examples, as well as other conditions and details, should not be construed to unduly limit this invention.

EXAMPLES

Coating Formulations:

The Coating Formulations 1 and 2 were prepared as solutions from the components listed in Tables 1 and 2. The pH of Coating Formulation 1 was about 8.5 and the pH of Coating Formulation 2 was about 7.2.

TABLE 1

Coating Formulation 1

| Component | Weight Percentage of Component in the Formulation | Source |
| --- | --- | --- |
| Water (from a MILLI Q water purification system) | 96.33% | EMD MILLIPORE Corp. (Billerica, MA) |
| Chlorhexidine digluconate (20% in water) [CAS No. 18472-51-0] | 0.32% | SIGMA-ALDRICH Co. (St. Louis, MO) |
| Triton X100 [CAS No. 9002-93-1] | 0.19% | SIGMA-ALDRICH Co. (St. Louis, MO) |
| Tricine [CAS No. 5704-04-1] | 1.72% | SIGMA-ALDRICH Co. (St. Louis, MO) |
| Sodium Hydroxide (4N) | 1.44% | VWR Corp. (Radnor, PA) |

TABLE 2

Coating Formulation 2

| Component | Weight Percentage of Component in the Formulation | Source |
| --- | --- | --- |
| Water (from a MILLI Q water purification system) | 99.47% | EMD MILLIPORE Corp. (Billerica, MA) |
| Chlorhexidine digluconate (20% in water) [CAS No. 18472-51-0] | 0.32% | SIGMA-ALDRICH Co. (St. Louis, MO) |
| Triton X100 [CAS No. 9002-93-1] | 0.21% | SIGMA-ALDRICH Co. (St. Louis, MO) |

Liquid Reagent Compositions:

The liquid reagent composition used in the following Examples comprises luciferin and a luciferase enzyme. The liquid reagent composition used in Examples 1-3 was prepared as a solution from the components listed in Table 3. The pH of the formulation was about 6.4. The total volume of liquid reagent composition contained in the sealed cuvette portion of each container was about 425 microliters.

TABLE 3

Liquid reagent composition

| Component | Weight Percentage of Component in the Formulation | Source |
| --- | --- | --- |
| Water (from a MILLI Q water purification system) | 77.6099% | EMD MILLIPORE Corp. (Billerica, MA) |
| ADA Free Acid [CAS No. 26239-55-4] | 0.0283% | SIGMA-ALDRICH Co. (St. Louis, MO) |

TABLE 3-continued

Liquid reagent composition

| Component | Weight Percentage of Component in the Formulation | Source |
|---|---|---|
| ADA Disodium Salt [CAS No. 41689-31-0] | 0.3081% | SIGMA-ALDRICH Co. (St. Louis, MO) |
| EDTA Disodium Salt Dihydrate [CAS No. 6381-92-6] | 0.0646% | SIGMA-ALDRICH Co. (St. Louis, MO) |
| Magnesium Acetate Tetrahydrate [CAS No. 16674-78-5] | 0.1862% | SIGMA-ALDRICH Co. (St. Louis, MO) |
| Sodium Azide [CAS No. 26628-22-8] | 0.0457% | SIGMA-ALDRICH Co. (St. Louis, MO) |
| D-Sorbitol [CAS No. 50-70-4] | 21.7106% | MOLEKULA LTD (Gillingham, UK) |
| Bovine Serum Albumin [CAS No. 9048-46-8] | 0.0457% | SIGMA-ALDRICH Co. (St. Louis, MO) |
| UltraGlo Luciferase (Type E140X) | 0.0009% (9 mg/L) | PROMEGA Corp. (Madison, WI) |
| Luciferin (Type XE160X) | 0.00003-0.00004% (0.3-0.4 mg/L) | PROMEGA Corp. (Madison, WI) |

The liquid reagent composition used in Comparative Examples 1-3 was the same as listed in Table 2 with the exception that sodium hydroxide (4N) was added as a pH-adjusting reagent to adjust the pH of the liquid reagent composition from 6.4 to 6.8.

Preparation of ATP Test Apparatuses:

An apparatus similar to the design described in FIG. 1A was used. The handling portion of the sampling device was fabricated from a polypropylene/TPE blend. The stem and sampling portion of the sampling device were fabricated (i.e., molded as a unitary part) using an acetal resin. The sampling device had an overall length of about 167 mm with the handling portion extending about 50.5 mm in length; the stem extending about 89.5 mm in length; and the sample collection ring element extending about 27 mm in length. The cavities in the sampling portion were positioned at least about 10 mm away from the stem. The cavities consisted of 11 spaced-apart indentations (approximately 0.3-0.4 mm deep) circling the sampling portion. The cavities were spaced apart over a distance of about 14.6 mm in the sampling portion of the sampling device with a spacing of about 0.85 mm between each cavity. A sharp conical shaped tip (about 2.4 mm in length) was located at the end of the sampling portion opposite the stem, as shown in FIG. 1A.

3M™ CLEAN-TRACE™ WATER ATP Test devices were obtained from the 3M Company. (St. Paul, Minn.). The pellet of freeze-dried enzyme located in the foil-sealed compartment of each test device was removed from the container and the liquid in the cuvette portion of the container was replaced with 425 microliters of the liquid reagent composition described in Table 3. In addition, the sampling portion of the sampling device was coated with one of the coating formulations described in Tables 1 and 2. The sampling device was coated by holding the handling portion of the sampling device and dipping the opposite end of the device into the coating solution to a point where all of the cavities were immersed in the coating solution. After the device was withdrawn from the coating solution, approximately 145 microliters of the coating solution remained on the sampling device. Warm air was used to dry the coating onto the sampling device.

Example 1

The ATP test apparatus described above was used. The sampling portion of the sampling device was coated with Coating Formulation 1 and dried as described above. The sampling device was removed from the ATP test apparatus and dipped into a vial containing 10 mL of $5 \times 10^{-9}$ M adenosine triphophate (ATP), commercially available from the Sigma-Aldrich Corporation. While the sampling portion was immersed in the ATP solution, gentle tapping of the sampling device against the side of the vial was used to dislodge any air bubbles from the cavities and facilitate acquisition of the predefined volume of sample liquid. After about 1-3 seconds of immersion, the sampling device was quickly removed from the vial and reinserted into the container. The sampling device retained about 145 microliters of the ATP solution. The handle of the sampling device was pressed in order to move the sampling device from the first operational position to the second operational position. The movement of the sampling device in the container caused the frangible seal to be broken and the sampling portion to be positioned in direct contact with the liquid reagent composition. The container was held in the vertical position and shaken rapidly from side to side (pendulum motion) for 10 seconds. After shaking the container, the cuvette portion of the apparatus was immediately inserted into a CLEAN-TRACE™ NG Luminometer (commercially available from 3M Company, St. Paul, Minn.) and measurements were recorded in relative light units (RLU). The RLU measurements were taken approximately every 10 seconds over a 70 second time period. This was accomplished by initiating a new reading for the luminometer immediately after the previous reading. Because the instrument takes approximately 10 seconds to obtain and present each new reading, this resulted in RLU measurements taken about every 10 seconds. All testing was conducted in an environmental chamber at 10° C. All materials and equipment were equilibrated in the chamber prior to testing. A total of five replicate samples were tested and the results are presented in Table 4.

Movement of the sampling device from the first operational position to the second operational position resulted in the pH of the liquid reagent composition in the cuvette increasing from a pH approximately 6.4 to a pH approximately 7.2.

Comparative Example 1

The same procedure was used as in Example 1 with the exception that the sampling device was coated with Coating Formulation 2 and the pH of the liquid reagent composition was 6.8. The RLU measurements were taken every 10 seconds over a 70 second time period. A total of five replicate samples were tested and the results are presented in Table 5.

TABLE 4

Sampling Device Coated with Coating Formulation 1 (Example 1)

| Time (seconds) | RLU Measurement at 10° C. | | | | |
|---|---|---|---|---|---|
| | Sample 1 | Sample 2 | Sample 3 | Sample 4 | Sample 5 |
| 10 | 13,646 | 16,141 | 13,922 | 12,895 | 17,277 |
| 20 | 13,682 | 17,547 | 14,971 | 13,331 | 18,053 |
| 30 | 13,436 | 17,565 | 14,894 | 13,241 | 17,997 |
| 40 | 13,303 | 17,439 | 14,780 | 13,118 | 17,783 |
| 50 | 13,220 | 17,219 | 14,623 | 13,033 | 17,578 |
| 60 | 13,100 | 17,046 | 14,548 | 12,915 | 17,364 |
| 70 | 12,992 | 16,936 | 14,380 | 12,801 | 17,180 |

TABLE 5

Sampling Device Coated with Coating Formulation 2 (Comparative Example 1)

| Time (seconds) | RLU Measurement at 10° C. | | | | |
|---|---|---|---|---|---|
| | Sample 1 | Sample 2 | Sample 3 | Sample 4 | Sample 5 |
| 10 | 6,667 | 6,048 | 5,049 | 4,200 | 5,046 |
| 20 | 8,892 | 7,903 | 7,615 | 6,404 | 7,671 |
| 30 | 9,794 | 8,718 | 8,653 | 7,405 | 8,656 |
| 40 | 10,199 | 9,015 | 9,114 | 7,904 | 9,107 |
| 50 | 10,342 | 9,198 | 9,273 | 8,136 | 9,284 |
| 60 | 10,395 | 9,146 | 9,326 | 8,180 | 9,363 |
| 70 | 10,377 | 9,099 | 9,324 | 8,237 | 9,365 |

Example 2

The same procedure as described in Example 1 was followed with the exception that the tests were conducted at 14° C. A total of five replicate samples were tested and the results are presented in Table 6.

Comparative Example 2

The same procedure was used as in Example 2 with the exception that the sampling device was coated with Coating Formulation 2 and the pH of the liquid reagent composition was 6.8. The RLU measurements were taken every 10 seconds over a 70 second time period. A total of five replicate samples were tested and the results are presented in Table 7.

TABLE 6

Sampling Device Coated with Coating Formulation 1 (Example 2)

| Time (seconds) | RLU Measurement at 14° C. | | | | |
|---|---|---|---|---|---|
| | Sample 1 | Sample 2 | Sample 3 | Sample 4 | Sample 5 |
| 10 | 18,874 | 19,415 | 20,888 | 22,388 | 20,630 |
| 20 | 18,920 | 20,266 | 21,430 | 22,749 | 20,624 |
| 30 | 18,761 | 20,134 | 21,268 | 22,548 | 20,447 |
| 40 | 18,530 | 19,908 | 21,106 | 22,297 | 20,161 |
| 50 | 18,316 | 19,961 | 20,837 | 22,106 | 19,899 |
| 60 | 18,180 | 19,527 | 20,639 | 21,924 | 19,738 |
| 70 | 18,040 | 19,352 | 20,666 | 21,776 | 19,597 |

TABLE 7

Sampling Device Coated with Coating Formulation 2 (Comparative Example 2)

| Time (seconds) | RLU Measurement at 14° C. | | | | |
|---|---|---|---|---|---|
| | Sample 1 | Sample 2 | Sample 3 | Sample 4 | Sample 5 |
| 10 | 8,961 | 9,630 | 8,110 | 7,171 | 7,174 |
| 20 | 11,003 | 11,520 | 10,085 | 9,025 | 9,036 |
| 30 | 11,628 | 12,065 | 10,537 | 9,574 | 9,504 |
| 40 | 11,771 | 12,278 | 10,560 | 9,758 | 9,755 |
| 50 | 11,815 | 12,268 | 10,528 | 9,824 | 9,782 |
| 60 | 11,773 | 12,260 | 10,486 | 9,821 | 9,824 |
| 70 | 11,703 | 12,204 | 10,453 | 9,774 | 9,788 |

Example 3

The same procedure as described in Example 1 was followed with the exception that the tests were conducted at 20° C. A total of five replicate samples were tested and the results are presented in Table 8.

Comparative Example 3

The same procedure was used as in Example 3 with the exception that the sampling device was coated with Coating Formulation 2 and the pH of the liquid reagent composition was 6.8. The RLU measurements were taken every 10 seconds over a 70 second time period. A total of five replicate samples were tested and the results are presented in Table 9.

TABLE 8

Sampling Device Coated with Coating Formulation 1 (Example 3)

| Time (seconds) | RLU Measurement at 20° C. | | | | |
|---|---|---|---|---|---|
| | Sample 1 | Sample 2 | Sample 3 | Sample 4 | Sample 5 |
| 10 | 18,605 | 21,358 | 21,553 | 19,799 | 18,697 |
| 20 | 18,571 | 21,166 | 21,451 | 19,657 | 18,501 |
| 30 | 18,331 | 20,938 | 21,248 | 19,497 | 18,334 |
| 40 | 18,192 | 20,788 | 21,141 | 19,367 | 18,179 |
| 50 | 18,039 | 20,619 | 20,931 | 19,221 | 18,019 |
| 60 | 17,953 | 20,465 | 20,745 | 19,097 | 17,873 |
| 70 | 17,785 | 20,310 | 20,622 | 18,963 | 17,753 |

TABLE 9

Sampling Device Coated with Coating Formulation 2 (Comparative Example 3)

| Time (seconds) | RLU Measurement at 20° C. | | | | |
|---|---|---|---|---|---|
| | Sample 1 | Sample 2 | Sample 3 | Sample 4 | Sample 5 |
| 10 | 11,749 | 11,306 | 10,638 | 11,625 | 10,098 |
| 20 | 12,392 | 12,872 | 11,700 | 13,547 | 11,452 |
| 30 | 12,530 | 13,083 | 11,922 | 13,828 | 11,662 |
| 40 | 12,496 | 13,113 | 11,908 | 13,779 | 11,687 |
| 50 | 12,382 | 13,039 | 11,903 | 13,770 | 11,639 |
| 60 | 12,345 | 13,010 | 11,844 | 13,726 | 11,602 |
| 70 | 12,305 | 12,925 | 11,827 | 13,659 | 11,561 |

Example 4

For the test samples of Examples 1-3 and the corresponding Comparative Examples 1-3, the percent increase in the RLU measurement between the first time point (10 seconds) and the second time point (20 seconds) was calculated using the following equation:

% Increase in RLU={[(RLU at 20 sec)−(RLU at 10 sec)]/(RLU at 10 sec)}×100

The mean percent increase (n=5) in the RLU measurement is reported in Table 10.

TABLE 10

| Example Number | Mean Percent Increase in the RLU Measurement (n = 5) | Standard Deviation |
|---|---|---|
| Example 1 | 4.9 | 3.3 |
| Comparative Example 1 | 43.9 | 10.8 |
| Example 2 | 1.8 | 1.8 |
| Comparative Example 2 | 23.7 | 2.6 |
| Example 3 | −0.7 | 0.3 |
| Comparative Example 3 | 11.8 | 4.2 |

Example 5

For the test samples of Examples 1-3 and the corresponding Comparative Examples 1-3, the mean time (n=5) to reach the maximum RLU measurement was determined. The results are reported in Table 11.

TABLE 11

| Example Number | Mean Time to the Maximum RLU Measurement in seconds (n = 5) |
| --- | --- |
| Example 1 | 22 |
| Comparative Example 1 | 62 |
| Example 2 | 18 |
| Comparative Example 2 | 48 |
| Example 3 | 10 |
| Comparative Example 3 | 34 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

What is claimed is:

1. An apparatus, comprising:
a container with an opening and a cuvette portion that is adapted to be operationally coupled to a luminometer;
a liquid reagent composition comprising luciferin, wherein the liquid reagent composition is disposed in a closed compartment, wherein the pH of the liquid reagent composition is about 6.8 or lower; and
a sampling device having a sampling portion;
wherein the sampling portion is adapted to acquire and releasably retain a predetermined volume of a liquid sample in one or more cavity that is not substantially defined by space between a plurality of fibers;
wherein the sampling device comprises a dry coating that includes an effective amount of a pH-adjusting reagent that, when contacted with the liquid reagent composition, changes the pH of the liquid reagent composition to 6.9 or higher.

2. The apparatus of claim 1, wherein the dry coating is disposed on the sampling portion of the sampling device.

3. The apparatus of claim 1, wherein the pH-adjusting reagent comprises a water-soluble reagent.

4. The apparatus of claim 1, wherein the sampling portion comprises a calibrated loop.

5. The apparatus of claim 1, wherein the closed compartment comprises a frangible wall.

6. The apparatus of claim 5, wherein the frangible wall is disposed in the container between the opening and the cuvette portion.

7. The apparatus of claim 1, wherein the sampling device comprises the closed compartment, wherein the sampling device further comprises a structure that selectively releases the fluid composition from the container.

8. The apparatus of claim 1, wherein the sampling portion comprises a foam material.

9. The apparatus of claim 1, wherein the pH-adjusting reagent comprises a buffer component selected from the group consisting of N-[2-hydroxyethyl] piperazine-N'-[2-ethanesulfonic acid], N-[tris(hydroxymethyl)methyl]glycine, and combinations thereof.

10. The apparatus of claim 1, wherein the pH-adjusting reagent is coated in the one or more cavity.

11. The apparatus of claim 1, wherein the coating further comprises a cell extractant.

12. The apparatus of claim 1, wherein the coating does not comprise an amount of a phosphate buffer component effective to change the pH of the liquid reagent composition to a pH of 6.9 or higher.

13. The apparatus of claim 1, wherein the predetermined volume is about 0.01 milliliters to about 0.25 milliliters.

14. A method, comprising:
using a sampling device to obtain a predetermined volume of a liquid sample;
wherein the sampling device comprises a sampling portion;
wherein the sampling portion is adapted to acquire and releasably retain a predetermined volume of liquid sample in one or more cavity, wherein the one or more cavity is not substantially defined by space between a plurality of fibers;
wherein the sampling device comprises a dry coating that includes an effective amount of a pH-adjusting reagent that, when contacted with a liquid reagent composition having a pH of about 6.8 or lower, changes the pH of the liquid reagent composition to 6.9 or higher;
wherein the liquid reagent composition comprises a luciferin;
contacting the predetermined volume of sample and the pH-adjusting reagent with a liquid reagent composition in a container to form a reaction mixture; and
using a luminometer to detect light emitted from the reaction mixture;
wherein the container comprises a cuvette portion adapted to be operationally coupled to the luminometer.

15. The method of claim 14, further comprising the step of agitating the predetermined volume of the sample and the liquid reagent composition in the container.

16. The method of claim 14, wherein the liquid reagent composition further comprises a luciferase enzyme.

17. The method of claim 14, wherein contacting the sampling device comprising the sample with liquid reagent composition comprises contacting the sampling device with the liquid reagent composition at a temperature within a range of 10° C. and 35° C., inclusive.

18. The method of claim 14, wherein, after contacting the sampling device with liquid reagent composition, a substantially steady-state amount of light is emitted from the composition in less than 20 seconds.

* * * * *